US010246729B2

(12) United States Patent
Van Loo et al.

(10) Patent No.: US 10,246,729 B2
(45) Date of Patent: Apr. 2, 2019

(54) PROCESS FOR THE RECOVERY OF BETAINE FROM MOLASSES

(75) Inventors: Jan Van Loo, Huldenberg (BE); Wolfgang Wach, Worms (DE)

(73) Assignee: TIENSE SUIKERRAFFINADERIJ N.V. (BE)

( * ) Notice: Subject to any disclaimer, the term of this patent is extended or adjusted under 35 U.S.C. 154(b) by 0 days.

(21) Appl. No.: 13/695,258

(22) PCT Filed: May 12, 2011

(86) PCT No.: PCT/EP2011/002357
§ 371 (c)(1),
(2), (4) Date: Oct. 29, 2012

(87) PCT Pub. No.: WO2011/141175
PCT Pub. Date: Nov. 17, 2011

(65) Prior Publication Data
US 2013/0071519 A1    Mar. 21, 2013

(30) Foreign Application Priority Data
May 12, 2010  (EP) .................................... 10005025

(51) Int. Cl.
| | | |
|---|---|---|
| A23L 29/30 | (2016.01) |
| C12P 13/04 | (2006.01) |
| C07C 227/40 | (2006.01) |
| C12P 13/00 | (2006.01) |
| C12P 19/00 | (2006.01) |
| C12P 19/18 | (2006.01) |
| C13K 13/00 | (2006.01) |
| A23K 20/163 | (2016.01) |
| A23L 33/22 | (2016.01) |

(52) U.S. Cl.
CPC ............ *C12P 13/04* (2013.01); *A23K 20/163* (2016.05); *A23L 29/30* (2016.08); *A23L 33/22* (2016.08); *C07C 227/40* (2013.01); *C12P 13/007* (2013.01); *C12P 19/00* (2013.01); *C12P 19/18* (2013.01); *C12Y 204/01099* (2013.01); *C12Y 302/01007* (2013.01); *C13K 13/00* (2013.01)

(58) Field of Classification Search
CPC ....... C04B 24/10; A23L 1/09; A61K 2300/00; A61K 8/60; B01D 15/362; B01D 2215/023; B01D 15/1864; B01D 15/1821; G01N 30/02; C07H 3/06; C12P 19/18; C12P 13/04; C13K 13/007; C13B 20/14; C13B 35/06; C13B 20/144; C13B 20/00
USPC ... 426/48, 490, 658, 16, 321, 548, 592, 656, 426/599, 615, 868; 210/656; 536/127
See application file for complete search history.

(56) References Cited

U.S. PATENT DOCUMENTS

| | | | |
|---|---|---|---|
| 3,806,363 A | 4/1974 | Takasaki ..................... 127/46 A |
| 3,884,714 A * | 5/1975 | Schneider et al. ........... 127/46.2 |
| 3,898,328 A | 8/1975 | Beigler .................. A61K 33/00 |
| 4,359,430 A | 11/1982 | Heikkila et al. ......... 260/501.13 |
| 5,127,957 A * | 7/1992 | Heikkila et al. ................. 127/47 |
| 5,756,132 A | 5/1998 | Rebhan .............................. 426/2 |
| 6,348,222 B1 | 2/2002 | Silveira ............................ 426/2 |
| 2009/0056707 A1* | 3/2009 | Foody ..................... B01J 39/04 127/46.2 |

FOREIGN PATENT DOCUMENTS

| | | | |
|---|---|---|---|
| BR | PI0705359 | 12/2009 | ............. C12P 19/00 |
| CN | 1974777 | 6/2007 | ............. C12P 19/00 |
| EP | 0 345 511 | 5/1989 | ............... C13J 1/06 |
| EP | 1298204 | 4/2009 | ............. C12N 9/10 |
| FR | 2851425 | 8/2004 | ............. A23L 1/30 |
| JP | H03209354 | 9/1991 | |
| JP | 2005530850 | 10/2005 | |
| WO | WO2004002938 | 1/2004 | |
| WO | WO 2005/051102 | 6/2005 | ............. A23L 1/30 |
| WO | WO2007071727 | 6/2007 | ............... C13J 1/06 |
| WO | WO2011141175 | 11/2011 | ............. C12P 13/00 |
| WO | WO2013072048 | 5/2013 | ............. C12P 19/16 |

OTHER PUBLICATIONS

Gramblicka, M. et al. J. Chem. Eng. Data; 52: 345-350 (2007).*
Ghazi et al. J. Agric.Food Chem. 54: 2964-2968 (2006) (Year: 2006).*
Iraj Ghazi et al. "Beet Sugar Syrup and Molasses as Low-Cost Feedstock for the Enzymatic Production of Fructo-oligosaccharides" *Journal of Agricultural and Food Chemistry*, vol. 54, No. 8, 2006 pp. 2964-2968 (8 pgs).
International Search Report issued in corresponding PCT application serial No. PCT/EP2011/002357, dated Aug. 19, 2011 (3 pgs).
"Production of sweetener containing fructooligosaccharides from sugar beet molasses" article, Journal article, with English abstract, 1989 (9 pgs).
Japanese Office Action (w/translation) issued in application No. 2015-151438, dated Jun. 7, 2016 (5 pgs).
Fujisaki et al., "Production Test of Sweetener Containing Fructooligosaccharides from Sugar Beet Molasses," Research Center of Nippon Beet Sugar Mfg. Co., Ltd., Obihiro, 080, Japan, Seito Gijutsu Kenkyu Kaishi (1989), (37), 27-32 (14 pgs).
Bertram et al., "NMR-based metabonomic studies reveal changes in the biochemical profile of plasma and urine from pigs fed high-fibre rye bread," British Journal of Nutrition, vol. 95, 2006, pp. 955-962 (8 pgs).

(Continued)

*Primary Examiner* — Hamid R Badr
(74) *Attorney, Agent, or Firm* — Hayes Soloway P.C.

(57) ABSTRACT

A process for the recovery of betaine from a molasses comprises a conversion step, in which the molasses is subjected to the action of an enzyme having endo-inulinase activity and/or fructosyltransferase activity, to form a fructan-containing molasses (fructan-molasses); a separation step, in which the fructan-molasses is subjected to a chromatographic separation, thereby obtaining a betaine-containing fraction.

6 Claims, 1 Drawing Sheet

(56) References Cited

OTHER PUBLICATIONS

International Search Report issued in application No. PCT/EP2014/001748, dated Mar. 12, 2015 (4 pgs).
Metzler-Zebeli et al., "Effects of betaine, organic acids and inulin as single feed additives or in combination on bacterial populations in the gastrointestinal tract of weaned pigs," Archives of Animal Nutrition, vol. 63, No. 6, 2009, abstract only (4 pgs).
Norman et al., "The Production of Fructooligosaccharides from Inulin or Sucrose Using Inulinase or Fructosyltransferase from *Aspergillus ficuum*," Denpun Kagaku, vol. 36, No. 2, 1989, pp. 103-111, abstract only (3 pgs).
PCT Written Opinion issued in application No. PCT/EP2014/001748, dated Dec. 26, 2016 (4 pgs).
International Preliminary Report on Patentability issued in application No. PCT/EP2014/001748, dated Dec. 27, 2016 (5 pgs).
Office Action issued in U.S. Appl. No. 15/321,735, dated Apr. 26, 2018 (13 pgs).
Office Action issued in U.S. Appl. No. 15/321,735, dated Sep. 27, 2017 (32 pgs).

* cited by examiner

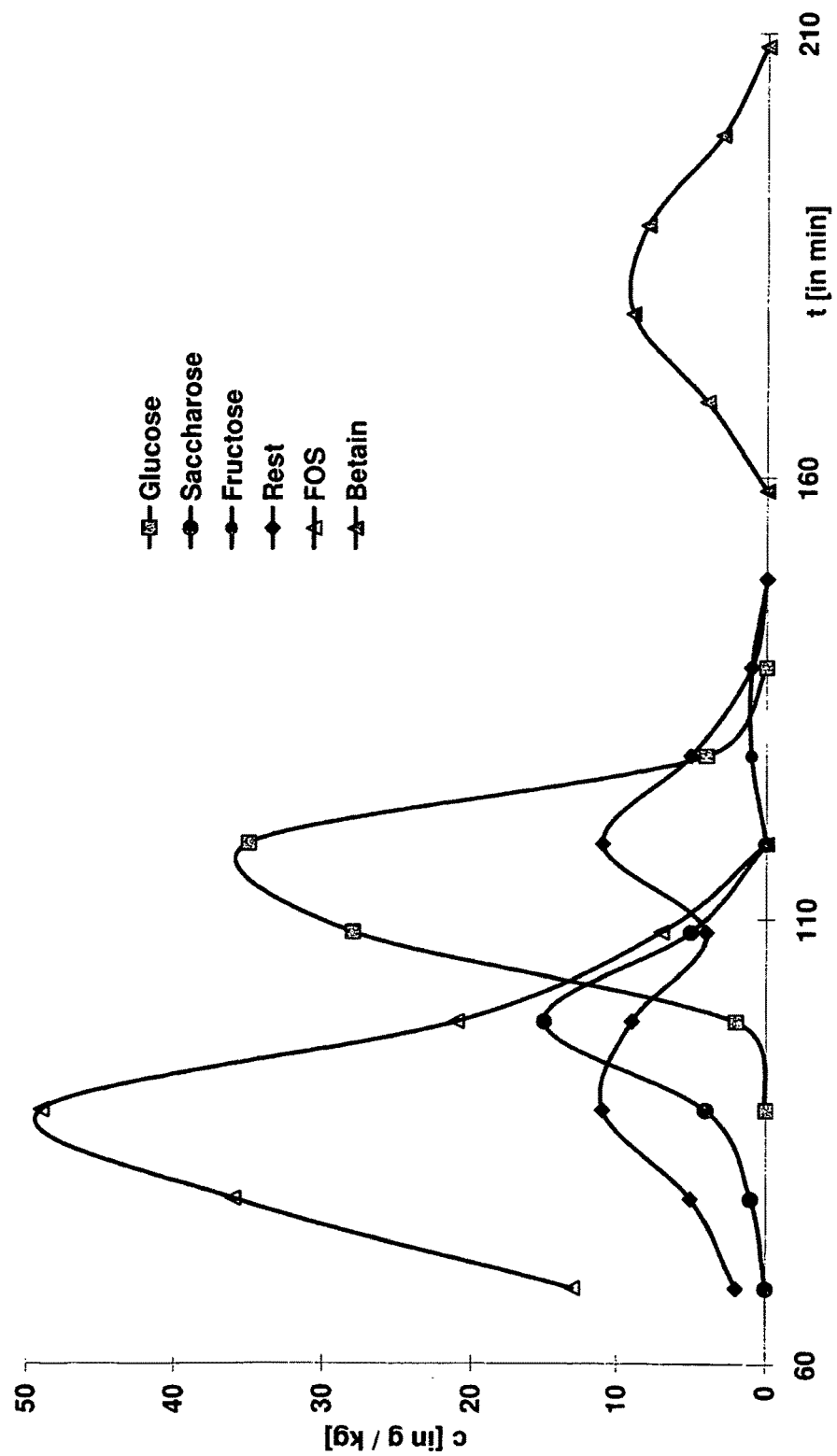

PROCESS FOR THE RECOVERY OF BETAINE FROM MOLASSES

BACKGROUND OF THE INVENTION

The invention relates to a process for the recovery of betaine from a molasses.

Such a process is known from U.S. Pat. No. 5,127,957. In the known process, a feed solution of beet molasses is fed into a simulated moving bed chromatographic system. Water is used as eluent. The chromatographic separation leads to the formation of various fractions, a.o. a fraction with increased betaine content and a fraction with increased sucrose content. In Example 1 of U.S. Pat. No. 5,127,957, the fraction with increased betaine content has 70.9 wt. % betaine (on dry matter) and 11.1 wt. % sucrose (on dry matter); the fraction with increased sucrose content has 86.6 wt. % sucrose (on dry matter) and 3.3 wt. % betaine (on dry matter).

A disadvantage of the known process is that the separation of betaine from the other fractions in the molasses is not always optimal.

SUMMARY OF THE INVENTION

It is an objective of the present invention to reduce the said disadvantage.

The objective is achieved in that the process comprises:
a conversion step, in which the molasses is subjected to the action of a fructan-forming enzyme, to form a fructan-containing molasses (fructan-molasses); and
a separation step, in which the fructan-molasses is subjected to a chromatographic separation, thereby obtaining a betaine-containing fraction.

It is an advantage of the process of the present invention that a betaine-containing fraction of high purity can be obtained more efficiently.

It is a further advantage of the process of the present invention that an important rest-fraction the process, i.e. the fructan-containing fraction as compared to a sucrose-containing fraction in the known process, can have a higher value than the corresponding sucrose-containing fraction of the known process.

DETAILED DESCRIPTION OF THE INVENTION

Iraj Ghazi et al. disclose in J. Agric. Food Chem., 2006, 54 (8), pp 2964-2968 how sugar syrup and molasses from beet processing were assayed as low-cost and available substrates for the enzymatic synthesis of fructo-oligosaccharides (FOSs). A commercial pectinase (Pectinex Ultra SP-L, from *Aspergillus aculeatus*) characterized by the presence of a transfructosylating activity was used as a biocatalyst.

The process of the invention relates to the recovery of betaine. As meant herein, betaine is used in its meaning of glycine betaine or N,N,N-trimethylglycine, a zwitterion found a.o. in sugar beets (*Beta vulgaris*) and having structural formula (I):

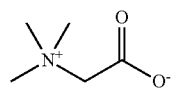

(I)

As is known, betaine has a number of functions in mammals, such as being a contributor to osmotic pressure and to function as methyl donor. These functions have led to the circumstance that there is a market for betaine, and it is thus desirable to obtain betaine as a product in an efficient way. One known group of sources of betaine is that of betaine-containing molasses, such as for example sugar beet molasses. The term molasses as used herein has its common meaning of being a by-product formed in a process for the preparation of sucrose, in particular in the crystallisation stages; furthermore, the molasses as used in the process according to the invention should contain betaine. As used herein, the term molasses refers to the molasses as obtained in the process for the preparation of sucrose, or to a diluted form thereof, whereby the dilution is preferably done with an aqueous phase. Preferably, the molasses is sugar beet molasses. As is known, sugar beet molasses can typically contain, based on total weight of the undiluted form, between 45 and 65 wt. % of sucrose, typically between 3 and 8 wt. % of betaine, typically between 6 and 10 wt. % of amino acids, smaller amounts of about 1 wt. % of fructose and glucose, and a significant amount of other compounds such as (in)organic salts.

In the process according to the invention, the molasses is subjected to the action of a fructan-forming enzyme. This may be achieved by means as such known. The molasses may be present as such or in diluted form; preferably, the molasses is present in diluted form, the dilution preferably having been done with water. If a certain dilution, or an increase of dilution, leads to a reduction of the efficiency of the enzyme used, then the benefit of dilution should be balanced against the efficiency reduction by the skilled person in routine fashion in order to establish the optimum for the specific circumstances. In one embodiment, the appropriate enzyme is in free form and is thoroughly mixed with the molasses; the enzyme-containing molasses is brought to conditions of temperature and pH such that the enzyme shows appreciable activity. In another embodiment, the enzyme is available in immobilized form, and the molasses is made to flow along the immobilized enzyme while also having been brought to appropriate conditions of temperature and pH.

The enzyme used in the process according to the invention should be able to catalyse the formation of fructans from sucrose. Free glucose may be formed as by-product.

The term fructan as used herein has its common meaning of being a generic term that relates to a carbohydrate material consisting mainly of fructosyl-fructose links with optionally a glucose starting moiety. The meaning of fructan encompasses the more specific compounds inulin—wherein the fructosyl-fructose links are mainly of the β(2→6) type—and levan—wherein the fructosyl-fructose links are mainly of the β(2→6) type. Both inulins and levans can be linear or branched, and both can be in polydisperse form, i.e. in the form of a mixture of various degrees of polymerisation, or in homodisperse form.

Inulin is usually polydisperse, i.e. a mixture of compounds of various chain lengths whereby the degree of polymerisation (DP) of the individual compounds can range from 2 to 100 or higher. The term fructo-oligosaccharide—abbreviated as FOS—as used herein indicates a specific form of an inulin material, either monodisperse or polydisperse, whereby the DP of the individual compounds ranges from 2 to 10, in practice often from 2 to 9, or from 2 to 8 or from 2 to 7. Commercially available FOS is usually a polydisperse material having a number-averaged degree of polymerisation ($\overline{DP}$) of about 2 to 5.

In practice, FOS is also referred to as oligofructose. As used herein, the terms fructo-oligosaccharide and oligofructose are considered to be synonyms.

The formation of fructan from sucrose may be achieved by selecting an enzyme having fructosyltransferase activity. Such enzymes are as such known, for instance as categorised under enzyme category number EC 2.4.1.99 or EC 2.4.1.9. An early disclosure of such an enzyme is in "The Production of Fructooligosaccharides from Inulin or Sucrose Using Inulinase or Fructosyltransferase from *Aspergillus ficuum*", Barrie E. Norman & Birgitte Højer-Pedersen, Denpun Kagaku vol 36, No. 2, pp 103-111 (1989).

Furthermore, it is known that some β-fructofuranosidases or invertases, i.e. enzymes categorised under EC 3.2.1.26, can also have fructosyltransferase activity and thus could be suitable in the process according to the invention.

Moreover, also enzymes having an endo-inulinase activity—such as enzymes classified under EC 3.2.1.7—may in the presence of sucrose give rise to the formation of fructans such as FOS, in particular if they act in a mixture having a high sucrose content of 40 or 50 wt. % sucrose or higher.

Yet furthermore, enzymes having levansucrase activity—such as enzymes classified under EC 2.4.1.10—can be suitable for use in the method according to the invention.

One example of a preferred enzyme for use in the conversion step of the invention is the endo-inulinase Novozyme 960 (supplier: Novozymes). Another example of a preferred enzyme for use in the conversion step of the invention is Pectinex Ultra SP-L (supplier: Novozymes). It is according to the invention also possible that the enzyme constitutes a combination of two or more enzymes having fructosyltransferase and/or endo-inulinase activity.

In a main embodiment of the invention, the molasses is brought in contact with an enzyme capable of catalyzing the formation of fructo-oligosaccharide (FOS) from sucrose. This main embodiment thus relates to:
  a conversion step, in which the molasses is subjected to the action of an enzyme having endo-inulinase activity and/or fructosyltransferase activity, to form a fructo-oligosaccharide-containing molasses (FOS-molasses);
  a separation step, in which the FOS-molasses is subjected to a chromatographic separation, thereby obtaining a betaine-containing fraction.

The amount of enzyme needed in the process according to the invention depends on various—as such known—factors such as process temperature, amount of raw materials, pH, allowable process duration, and desired conversion rates. These and other relevant factors may be determined for the process of the invention by the person skilled in the art following the generally accepted procedures in this technical field.

In the process according to the invention, the enzyme is allowed to act on the molasses for a period of time that is sufficiently long to create a fructan-containing molasses, preferably a FOS-containing molasses. The duration of execution of this step according to the invention is mainly chosen in function of the amount of fructan, preferably FOS that is desired. As the skilled person knows, this duration is often in the range between 0.5 or 1 and 72 hours, preferably between 5 and 50 hours, more preferably between 12 and 36 hours, during which a fructan-containing molasses (fructan-molasses), preferably a FOS-containing molasses (FOS-molasses) is formed.

It is preferred that in the conversion step, between 5 wt. % and 100 wt. % of the sucrose in the molasses is converted. More preferably, at least 10, 20, 30, 40, 50, 60, 70, 80, or 90 wt. % of the sucrose is converted. It is particularly preferred to convert essentially all sucrose. It was found that if the percentage of sucrose that is converted is increased, the subsequent recovery of betaine can be executed more efficiently.

Upon completion of the formation of the fructan-molasses, preferably the FOS-molasses, and in case a free, non-immobilized enzyme was used and mixed into the molasses, it may be desirable to ensure that the enzyme is deactivated. If this is the case, then an enzyme deactivating step may be implemented. The deactivation of the enzyme may be achieved by methods that are as such known and may differ for each specific type of enzyme. An example of such a method of deactivation is an increase in temperature—to a level of for example about 80, 85 or 90° C.—followed by a residence time of between 5 and 30 minutes at such an increased temperature. A further benefit of exposure at such a temperature is that the amounts of any bacteria that may be present are reduced.

In the process of the invention, a separation step is done on the fructan-molasses. The separation step is executed either during the conversion step or subsequent to the conversion step. Preferably, the separation step is executed subsequent to the conversion step. In the separation step, the fructan-molasses is subjected to a chromatographic separation. As is known, the subjection of a material to a chromatographic separation can lead to the splitting of the material into various fractions. The separation according to the invention should be done such that a betaine-containing fraction is formed. It is known to the person skilled in the art that the particular choice of the stationary phase in the chromatographic separation can influence the performance of the separation. The chromatographic separation may be executed by means that are as such known, such as the passing of the fructan-molasses over a resin.

In a main embodiment of the invention, the separation step is done via ion-exchange chromatography. As is known, a variety of ion-exchange chromatography technologies is available, such as resin-based ion-exchange chromatography, possibly in combination with size-exclusion mechanisms; also here, a variety of resins is available for this purpose. In one preferred embodiment of the process of the invention, a strong acid cation exchange resin is chosen. It was also found that if a cation exchange resin is chosen, the choice of cation can influence the separation efficiency. In one embodiment of the invention, cation exchange resins essentially in the sodium form are preferred. In this embodiment it is preferred to ensure that the sodium ions are not replaced to any great extent, preferably by no more than 50, 40, 30, 25, or even by no more than 20 or 15% by other ions such as potassium, as this may influence the separation efficiency. Thus, in case the separation step is to be done with a cation exchange resin whereby the type cation (for example, sodium) is significantly relevant to the separation efficiency and the fructan-molasses contains significant amounts of other ions (for example, potassium ions), it is preferred to implement an ion exchange and/or removal step on the molasses or on the fructan-molasses prior to the separation step. Such steps are as such known, such as for example via size-exclusion chromatography or electrodialysis.

It is thus preferred that prior to the separation step the molasses or the fructan-molasses is subjected to an ion-exchange step, whereby the amount of those cations in the molasses or the fructan-molasses that are different from the cation in which form the cation exchange resin is, is reduced; preferably this reduction is by at least 50%, more preferably by at least 75%, 80%, 85%, 90%, or even by at least 95%.

As is known in case a resin is used in the separation step, a certain routine optimization may be needed in order to choose the optimal type of resin, e.g. by varying the degree of cross-linking in the resin.

Preferably, the chromatographic separation is done in a simulated moving bed (SMB) system, or further developments of SMB systems such as a Sequential Simulated Moving Bed (SSMB) or an Improved Simulated Moving Bed (ISMB). This has the advantage that the separation step and/or the recovery of a betaine-containing fraction may be done on a continuous basis.

It was found, surprisingly, that a betaine-containing fraction of high purity can be recovered from a fructan-molasses. Without wishing to be bound to any theory, it is contemplated that the behaviour of fructans, in particular FOS, and possibly also glucose in a chromatographic separation could be such that it exits in a sharper, less diffuse peak than that of sucrose, possibly also influencing thereby the elution behaviour of certain other compounds in favour of obtaining a high-purity betaine.

In the process of the invention, a betaine-containing fraction is obtained. As meant herein, a betaine-containing fraction means a fraction in which the ratio of betaine to the other dry-matter constituents is increased as compared to the fructan-molasses entering the separation step. Preferably, the ratio of betaine to the other dry-matter constituents is increased to at least 25:75, more preferably to 40:60, 50:50, 60:40, 70:30, 80:20, or even to at least 90:10 or 95:5.

The betaine-containing fraction or fractions as obtained in the process of the invention may, if so desired, be processed further by means that are as such known, such as for example by a concentration step in which the amount of eluent is reduced or even brought to essentially zero through means such as evaporation or membrane techniques.

The process of the invention can also lead to the obtaining of fructan-containing fractions. Due to the presence of fructans such as preferably FOS, such fractions may, even though their betaine content may be low, have considerable value in various applications such as animal feed. The invention thus also relates to a converted sugar beet molasses product, containing at least 10 wt. % (as measured on total carbohydrates dry substance) of fructans, preferably fructo-oligosaccharides, and at the same time at most 2.0, 1.0 or 0.5 wt. % betaine (as measured on the total dry substance of the converted sugar beet molasses product). The converted sugar beet molasses product of the invention is obtainable, preferably obtained, from a sugar beet molasses having a betaine content of preferably at least 2, 2.5, 3, 3.5, or even 4 wt. % (as measured on the total dry substance of the sugar beet molasses). Preferably, the converted sugar beet molasses product contains at most 25, 20, 15, 10, 5, 4, 3, 2, or even 1 wt. % sucrose (as measured on total carbohydrates dry substance). It is furthermore preferred that the converted sugar beet molasses product contains at least 15, 20, 25, 30, 35, 40, 45, or even 50 wt. % of FOS (as measured on total carbohydrates dry substance). Preferably, the converted sugar beet molasses product contains at most 0.4, 0.3, 0.2 or even 0.1 wt. % betaine (of total dry matter). Furthermore, the converted sugar beet molasses product contains at most 35, 30, 25, 20, 15, 10, or 5 wt. % glucose (as measured on total carbohydrates dry substance).

If so desired, the converted sugar beet molasses product of the invention may be processed further, for example with the purpose of obtaining fructans, in particular FOS, in essentially pure form.

In the Figures, FIG. 1 shows a graphical representation of the results of the separation step of Example 1.

The process of the invention will be illustrated by means of the following Example, whereby the Example should not be interpreted as limiting the scope of the invention.

EXAMPLE 1

1000 g of a sugar beet molasses with a solids content of 84% was diluted with water such that the molasses had a solids content of 57.6%; the sucrose content then was 38.5 wt. %. The pH of the molasses was adjusted from 8.1 to 6.2. Any pH adjustments in this Example were done using an aqueous solution of HCl (9%) or an aqueous solution of NaOH (4%). The temperature of the molasses was brought to 56° C. To the molasses, an amount of 591 µl of the enzyme Novozyme 960 was added. The molasses was kept at the conditions of pH 6.2 and 56° C. for a period of 24 hours, after which a FOS-molasses had been formed successfully. The amount of FOS was determined to be 51% (wt. % of total carbohydrates).

The FOS-molasses was fed into a batch column for chromatographic separation. The column was 100 cm tall and 5 cm in diameter, and filled for 98 cm with Dowex 99/320 resin in Sodium-form. As is known, this resin is a strong acid cation exchange resin. The eluent, water, was fed into the column at a rate of 10 ml/min; a sample of 70 ml of the FOS-molasses was fed into the column. Between a time frame of 69 minutes and 209 after sample injection, individual fractions were collected per 10 minutes and analysed.

The results are given in Table 1, and in graphical form in FIG. 1.

TABLE 1

| Time | Fructose | Glucose | Sucrose | FOS | Betaine | Rest |
|---|---|---|---|---|---|---|
| 69  | 0.0 | 0.0  | 0.0  | 13.0 | 0.0 | 2.0  |
| 79  | 0.0 | 0.0  | 1.0  | 36.0 | 0.0 | 5.0  |
| 89  | 0.0 | 0.0  | 4.0  | 49.0 | 0.0 | 11.0 |
| 99  | 0.0 | 2.0  | 15.0 | 21.0 | 0.0 | 9.0  |
| 109 | 0.0 | 28.0 | 5.0  | 7.0  | 0.0 | 4.0  |
| 119 | 0.0 | 35.0 | 0.0  | 0.0  | 0.0 | 11.0 |
| 129 | 1.0 | 4.0  | 0.0  | 0.0  | 0.0 | 5.0  |
| 139 | 1.0 | 0.0  | 0.0  | 0.0  | 0.0 | 1.0  |
| 149 | 0.0 | 0.0  | 0.0  | 0.0  | 0.0 | 0.0  |
| 159 | 0.0 | 0.0  | 0.0  | 0.0  | 0.0 | 1.0  |
| 169 | 0.0 | 0.0  | 0.0  | 0.0  | 4.0 | 0.0  |
| 179 | 0.0 | 0.0  | 0.0  | 0.0  | 9.0 | 0.0  |
| 189 | 0.0 | 0.0  | 0.0  | 0.0  | 8.0 | 0.0  |
| 199 | 0.0 | 0.0  | 0.0  | 0.0  | 3.0 | 0.0  |
| 209 | 0.0 | 0.0  | 0.0  | 0.0  | 0.0 | 1.0  |

Legend to Table 1
 Time=Time after sample injection in minutes
 Numerical values are concentrations in g/kg
 The fraction 'Rest' contains all dry-matter constituents besides the ones concretely identified in the Table (these are fructose, glucose, sucrose, FOS, and betaine); examples of compounds contained in the fraction 'Rest' are salts It follows clearly from the results that betaine is obtained in very high purity; the fractions obtained between minutes 169 and 199 contain essentially no sucrose or other compounds, whereas the FOS-containing fractions contain essentially no betaine.

The invention claimed is:

1. A process for the recovery of betaine from a sugar beet molasses said method comprising the steps of:

providing a starting material containing between 45 and 65 wt. % sucrose, between 3 and 8 wt. % betaine, between 6 and 10 wt. % amino acids, as well as fructose, glucose and inorganic salts, wherein the starting material comprises a sugar beet molasses by-product formed in a process for preparation of sucrose, a conversion step, in which the sugar beet molasses starting material is first subjected to the action of a fructan-forming enzyme, having endo-inulinase activity and/or fructosyltransferase activity, whereby at least 80 wt % of the sucrose contained in the sugar beet molasses is converted to form a fructo-oligosaccharide-containing molasses (FOS-molasses); and a separation step, in which the FOS-molasses from the conversion step is subjected to a chromatographic separation, thereby obtaining a betaine-containing fraction having a ratio of betaine to other dry-matter constituents of the FOS-molasses of at least 70:30, wherein:

prior to the separation step the FOS-molasses from the conversion step is heated to a temperature of between 80-90° C. and held at such temperature for between 5 and 30 minutes to deactivate the enzyme and reduce any bacteria that may be present in the FOS-molasses, the separation step is accomplished by ion-exchange chromatography in a simulated moving bed chromatography system, a cation exchange resin is used in the ion-exchange chromatographic separation step, and prior to the separation step the molasses or the fructan-molasses is subjected to an ion-exchange step, whereby the concentration of those cations in the molasses or in the fructan-molasses that are different from the cation exchange resin, is reduced by at least 90%.

2. The process according to claim 1, wherein the fruetan-forming enzyme is selected from the group consisting of an enzyme having endo-inulinase activity, an enzyme having fructosyltransferase activity, and a mixture thereof.

3. The process according to claim 1, wherein the cation exchange resin is in sodium form.

4. The process according to claim 1, wherein the concentration of the cations in the molasses or in the fructan-molasses that are different from the cation exchange resin is reduced by at least 95%.

5. The process according to claim 1, wherein the FOS-molasses from the conversion step is heated to a temperature of 85° C. for 5 to 30 minutes prior to the separation step.

6. The process according to claim 1, wherein the FOS-molasses from the conversion step is heated to a temperature of 90° C. for 5 to 30 minutes prior to the separation step.

* * * * *